(12) United States Patent
Lalo

(10) Patent No.: US 10,500,299 B2
(45) Date of Patent: Dec. 10, 2019

(54) ENCAPSULATED AIR FRESHENER FOR HOME AC

(71) Applicant: Ekaterina Lalo, Encino, CA (US)

(72) Inventor: Ekaterina Lalo, Encino, CA (US)

(*) Notice: Subject to any disclaimer, the term of this patent is extended or adjusted under 35 U.S.C. 154(b) by 66 days.

(21) Appl. No.: 15/647,115

(22) Filed: Jul. 11, 2017

(65) Prior Publication Data

US 2018/0140735 A1 May 24, 2018

Related U.S. Application Data

(60) Provisional application No. 62/334,869, filed on May 11, 2016.

(51) Int. Cl.
*A61L 9/12* (2006.01)
*B60H 3/00* (2006.01)
*F24F 3/12* (2006.01)

(52) U.S. Cl.
CPC .............. *A61L 9/12* (2013.01); *B60H 3/0028* (2013.01); *F24F 3/12* (2013.01); *A61L 2209/16* (2013.01)

(58) Field of Classification Search
CPC .......... A61L 9/12; A61L 2209/16; F24F 3/12; B60H 3/0028
See application file for complete search history.

(56) References Cited

U.S. PATENT DOCUMENTS

| 1,100,751 | A | * | 6/1914 | Lindstrom | A61L 9/122 |
| | | | | | 261/30 |
| 1,246,529 | A | * | 11/1917 | Bieder | A61L 9/122 |
| | | | | | 422/124 |
| 4,849,606 | A | | 7/1989 | Martens, III et al. | |
| 5,273,690 | A | | 12/1993 | McDowell | |
| 5,527,493 | A | | 6/1996 | McElfresh et al. | |
| 6,117,218 | A | | 9/2000 | Snyder et al. | |
| 6,749,672 | B2 | | 6/2004 | Lynn | |
| 2012/0079945 | A1 | | 4/2012 | Roberts | |
| 2016/0279279 | A1 | * | 9/2016 | Wonnacott | A61L 9/048 |

* cited by examiner

*Primary Examiner* — Sean E Conley
(74) *Attorney, Agent, or Firm* — Buche & Associates, P.C.; John K. Buche; Bryce A. Johnson

(57) ABSTRACT

An encapsulated air freshener device employing a forced air means to diffuse fragrant air throughout an environment from a cartridge that is housed in a perforated device. The device is configured to be attached to the grills of a vent of an AC unit and blend in seamlessly with the vent cover. The air freshener device is aesthetically pleasing, easy to install, and easy to maintain.

3 Claims, 2 Drawing Sheets

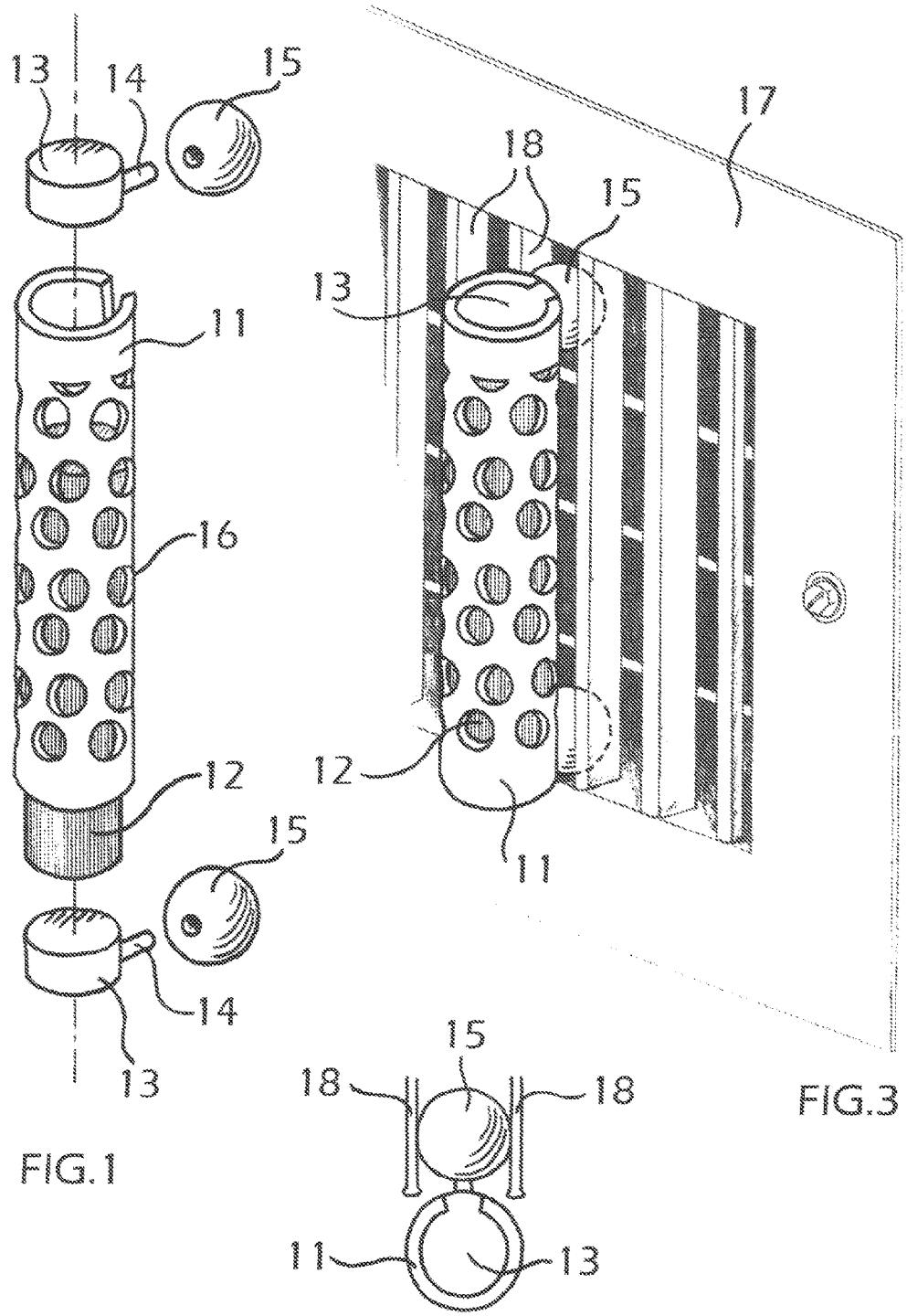

ENCAPSULATED AIR FRESHENER FOR HOME AC

CROSS-REFERENCE TO RELATED APPLICATIONS

This application claims the benefit and priority of U.S. Provisional Application No. 62/334,869 filed May 11, 2016, entitled "Encapsulated Air Freshener for Home AC."

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

REFERENCE TO AN APPENDIX SUBMITTED ON A COMPACT DISC AND AN INCORPORATED BY REFERENCE OF THE MATERIAL ON THE COMPACT DISC

Not applicable.

STATEMENT REGARDING PRIOR DISCLOSURES BY THE INVENTOR OR A JOINT INVENTOR

Reserved for a later date, if necessary.

BACKGROUND OF THE INVENTION

Field of Invention

The disclosed subject matter is in the field of air fresheners for air conditioning vents.

Background of the Invention

This relates to air fresheners, specifically to air freshener devices employing forced air which allow users to attach the device to an air vent grill or vent of a home or car air conditioning unit ("AC" or "HVAC System"). The most commonly used home air freshening devices are aerosol spray, incense sticks, diffusers, scented candles, or aromatic balls, which are placed in an area where the air is to be freshened. All of these air fresheners take up valuable space on various surfaces and detract from the appearance of the home. Another type of air freshening device includes the use of a housing that holds a volatile material in connection with an electrically heated vapor dispensing device. See U.S. Pat. No. 4,849,606 to Martens, III et al. None of the aforementioned devices use the forced air power from an HVAC system.

U.S. Pat. No. 5,527,493 to McElfresh shows a design for an air freshener device, which uses the air flow and attached directly to the air vent grill. This includes a housing and a reservoir of a volatile material, such as an air freshener fragrance. McElfresh discloses an air freshener that dispenses a fragrance into the atmosphere of an enclosed area and is attached to the air vent grill by alligator clips. However, its effectiveness is too low due to its small dimensions and alligator clips tend to lose their grip over time. Additionally, the back of the housing is not perforated and blocks the essential air flow from the AC unit.

U.S. Pat. No. 5,273,690 to McDowell discloses an air freshener device that is a combination of a forced air source with a carrier that has a plurality of fragrance of scented emitting ingredients arranged in separate cells or compartments that are arranged in rows and/or columns. Attachment elements secure the carrier to supporting structure so that released ingredient will enter the stream of forced air for distribution through a room. McDoweli̇s effectiveness is too low due to its flat body, which only holds a very small amount of the fragrant substance and, accordingly, should be replaced frequently to keep air fresh and scented. Additionally, McDowell's apparatus is aesthetically unpleasing and flimsy since the carrier strips wave when in operation, which also makes unnecessary noise. On the other hand, the present invention is more aesthetically pleasing because it blends in with the vents as it is firmly attached into a vent.

U.S. Pat. App. No. 2012/0079945 to Roberts discloses an air freshener dispensing cover which covers an AC grate or vent and causes the airstream from an AC unit to be filtered through the cover and pass over a fragrance oil cartridge. This cover completely covers an air vent and features a more complicated installation process than the present invention. Also, Roberts affects the amount of forced air that is flowing into an area, so it lowers the efficiency and increases the time to cool or heat an environment.

Both U.S. Pat. No. 6,749,672 to Lynn and U.S. Pat. No. 6,117,218 to Snyder et al. show scenting devices for use with airflow conduits. These scenting devices are made from a special material and attached to an air filter of ventilation cover in existing heating, ventilating, or HVAC systems. However, these devices have to be installed inside the HVAC system and it is more complicated to install and maintain than the present invention.

Therefore, there is a need for an encapsulated air freshener for AC units with a forced direct air flow that provides an aesthetically pleasing design, easy installation and maintenance, and that does not significantly alter the efficiency of an AC unit.

Accordingly several advantages to the present invention is as follows: (a) it provides a means of odorizing an enclosed area such as room, office, and cabinet from forced air flow from an HVAC system; (b) it provides an air freshener with that does not require electricity or an electrical outlet to be employed; (c) it is user friendly because it is easy to install and maintain; (d) the perforated design of the housing integrates with general air vent design and does not disrupt the interior design of an environment; and, (e) the use of this device has therapeutic benefits for members of the household based on different scented fragrances. Further advantages will become apparent from the following description and the accompanying drawings.

SUMMARY OF THE INVENTION

In view of the foregoing, an object of this invention is to provide an improved encapsulated air freshener for AC units based on placing the perfumed cartridge in a unique housing that has attachment units, which enable a user to place the device on the vent of an AC unit to spread a fragrance from the forced air that is being emitted. The air freshener employs the forced air from the AC unit to diffuse the fragrance, that is housed in the device, throughout am enclosed area. This invention keeps the home smelling fresh with a pleasant smelling scent that is activated and circulated by the direct air flow, while masking odors.

BRIEF DESCRIPTION OF THE SEVERAL VIEWS OF THE DRAWINGS

Other objectives of the disclosure will become apparent to those skilled in the art once the invention has been shown and described. The manner in which these objectives and other desirable characteristics can be obtained is explained in the following description and attached figures in which:

FIG. 1 is an exploded view of the air freshener.

FIG. 2 is a top view of the air freshener installed between air vent grills.

FIG. 3 is a perspective view of the air freshener installed in an air vent grill.

Figure 4:
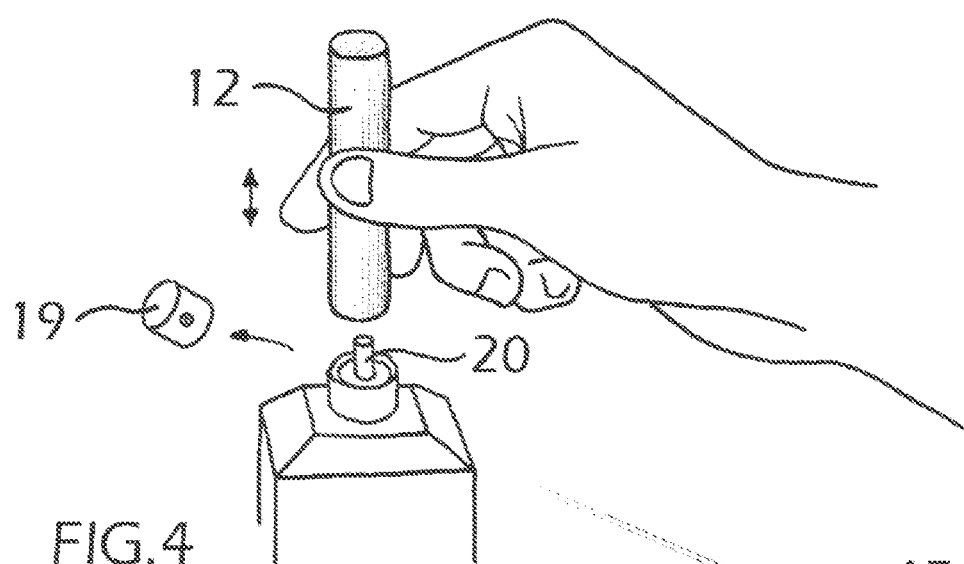
FIG. 4 is a perspective view of the filling process by sucking perfume liquid from the bottle to the cartridge.

In the figures, the following components are represented by the associated reference numeral:

11 tube;
12 cartridge;
13 closing cup;
14 pin;
15 attachment units;
16 perforation;
17 AC vent cover;
18 grills;
19 upper part of the perfume's bottle spray mechanism; and,
20 tube of the perfume's bottle spray mechanism.

It is to be noted, however, that the appended figures illustrate only typical embodiments of this invention and are therefore not to be considered limiting of its scope, for the invention may admit to other equally effective embodiments that will be appreciated by those reasonably skilled in the relevant arts. Also, figures are not necessarily made to scale but are representative.

DETAILED DESCRIPTION OF PREFERRED EMBODIMENTS

Disclosed is an encapsulated air freshener for air conditioning vents and grills.

FIG. 1 is a perspective view of an encapsulated air freshener device for an HVAC system, or other air ventilation system. Referring to FIG. 1, in a preferred embodiment, the device is comprised of: a tube (11) a cartridge (12); closing cups (13); and attachment units (15). The tube (11) may be produced in various shapes, including, but not limited to, cylindrical, square, or triangular shapes. Furthermore, the tube (11) contains a plurality of perforations (16) which allow to air flow through the air freshener device. The perforation design (16) is not limited to the certain type of design and can be done in any shape and any form. The tube (11), may be comprised of a metal, plastic, ceramic, or any other rigid and durable material.

Still referring to FIG. 1, the closing cups (13) cap the top and bottom of the tube (11), so that the cartridge (12) does not fall out. The closing cups (13) also have pins (14), which receive the attachment units (15). The attachment units (15) may be rubber, silicon, or any other material that can be compressible or manipulated to fit through a vent grill (18) and regain its shape to stay in the vent grill (18) and hold the air freshener device in place. The attachment units (15) may also be any shape, such as, a ball or a prism. In another embodiment, the attachment unit (15) can be a clip or any other attachment device.

The tube (11) is designed to match the measurements and color of an AC vent cover. The cartridge (12) may be made of a durable and highly absorbed material such as pressed rayon polyester blend, ceramic, cellulose acetate, pressed cotton, or cardboard. The shape of the cartridge (12) is designed to fit within the tube (11). The cartridge (12) may be sprayed or soaked in various scented liquids such as perfume, aromatic oils, diffuser liquid, etc. The cartridge (12) material allows consumers to immerse it with their favorite scents such as perfumes, colognes and oils.

FIG. 2 is a top view of the air freshener device secured between air vent grills (18). As shown in FIG. 2, the air freshener is attached to the air vent by attachment units (15) squeezed between air vent grills (18).

FIG. 3 is a perspective view of the air freshener device installed in the grills of an air vent. Referring to FIG. 3, when an air unit is on, the forced air is flowing through the perforated holes of the tube and the cartridge disposed within the tube. The forced air will disperse the fragrance in the cartridge throughout the environment.

In operation, a user may soak or spray a cartridge (12) with a desired fragrance. FIG. 4 displays one embodiment of a fragrance filling process for a cartridge (12). Referring to FIG. 4, a preferred liquid filling process may be as follows: take off an upper part of the perfume's bottle spray mechanism (19); adjust the cartridge (12) above the small tube of the spray mechanism (20); and, through a press and release, motion suck the liquid of the desired perfume into the cartridge (12).

After the perfumed cartridge (12) is ready, a user caps one end of the tube (11) and inserts the cartridge into the tube (11). A user then caps the other end of the tube with the closing cups (13) with the attachment units (15) attached. A user then installs the air freshener device by pushing the attachment units (15) the between the vent grills (18) of the AC vent cover (17).

Figure 5:
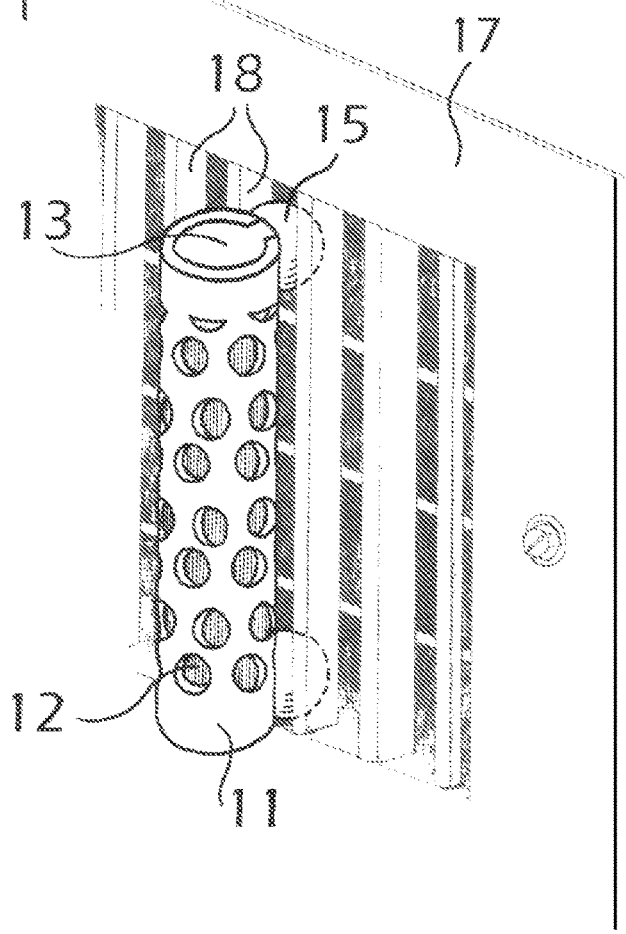
FIG. 5 is a perspective view of the air freshener installed between air vent grills.

FIG. 5 is a perspective view of the air freshener device installed in the grills of an air vent.

A user can add as many another encapsulated air freshener to the same or another air vent to make the fragrance in an area stronger.

The air freshener unit may come in a variety of different sizes and used in a home AC unit or in the air vent of a car.

Although the method and apparatus is described above in terms of various exemplary embodiments and implementations, it should be understood that the various features, aspects and functionality described in one or more of the individual embodiments are not limited in their applicability to the particular embodiment with which they are described, but instead might be applied, alone or in various combinations, to one or more of the other embodiments of the disclosed method and apparatus, whether or not such embodiments are described and whether or not such features are presented as being a part of a described embodiment. Thus the breadth and scope of the claimed invention should not be limited by any of the above-described embodiments.

Terms and phrases used in this document, and variations thereof, unless otherwise expressly stated, should be construed as open-ended as opposed to limiting. As examples of the foregoing: the term "including" should be read as meaning "including, without limitation" or the like, the term "example" is used to provide exemplary instances of the item in discussion, not an exhaustive or limiting list thereof, the terms "a" or "an" should be read as meaning "at least one," "one or more," or the like, and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that might be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases might be absent. The use of the term "assembly" does not imply that the components or functionality described or claimed as part of the module are all configured in a common package. Indeed, any or all of the various components of a module, whether control logic or other components, might be combined in a single package or separately maintained and might further be distributed across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives might be implemented without confinement to the illustrated examples. For example, block diagrams and their accompanying description should not be construed as mandating a particular architecture or configuration.

All original claims submitted with this specification are incorporated by reference in their entirety as if fully set forth herein.

I claim:

1. A method of introducing a fragrance into an environment comprising:

obtaining an air vent with grills;

obtaining an air freshener device comprising: a tube with a first end and a second end, wherein the tube is perforated; a cartridge that is configured to fit within the tube; at least one closing cup, wherein the closing cup is configured to cap the first or second end of the tube; and, at least one attachment unit that is fixed to at least one closing cup;

introducing a fragrance to the cartridge;

inserting the cartridge into the tube that is capped on one end;

capping the other end of the tube;

inserting the attachment units into the grill of an air vent;

turning on an air conditioning unit, whereby the forced air flows through the perforated holes of the tube and the cartridge to disperse the fragrance throughout the environment; and, wherein the attachment unit is a ball.

2. A method of introducing a fragrance into an environment comprising:

obtaining an air vent with grills;

obtaining an air freshener device comprising: a tube with a first end and a second end, wherein the tube is perforated; a cartridge that is configured to fit within the tube; at least one closing cup, wherein the closing cup is configured to cap the first or second end of the tube; and, at least one attachment unit that is fixed to at least one closing cup;

introducing a fragrance to the cartridge;

inserting the cartridge into the tube that is capped on one end;

capping the other end of the tube;

inserting the attachment units into the grill of an air vent;

turning on an air conditioning unit, whereby the forced air flows through the perforated holes of the tube and the cartridge to disperse the fragrance throughout the environment; and, wherein the attachment unit is silicone.

3. A method of introducing a fragrance into an environment comprising:

obtaining an air vent with grills;

obtaining an air freshener device comprising: a tube with a first end and a second end, wherein the tube is perforated; a cartridge that is configured to fit within the tube; at least one closing cup, wherein the closing cup is configured to cap the first or second end of the tube; and, at least one attachment unit that is fixed to at least one closing cup;

introducing a fragrance to the cartridge;

inserting the cartridge into the tube that is capped on one end;

capping the other end of the tube;

inserting the attachment units into the grill of an air vent;

turning on an air conditioning unit, whereby the forced air flows through the perforated holes of the tube and the cartridge to disperse the fragrance throughout the environment; and, wherein the attachment unit is fixed to the closing cup via a pin.

* * * * *